US00PP12047P2

(12) United States Plant Patent
Nagatomi et al.

(10) Patent No.: US PP12,047 P2
(45) Date of Patent: Aug. 14, 2001

(54) **VARIETY OF *CYTISUS SCOPARIUS L.* PLANT NAMED 'MEI ROAD'**

(75) Inventors: Shigeki Nagatomi, Ibaraki; Hiroyuki Anzai; Kazuko Katsumata, both of Kanagawa, all of (JP)

(73) Assignees: National Institute of Agrobiological Resources, Ministry of Agriculture, Forestry and Fisheries, Tsukuba; Meiji Seika Kaisha, Ltd., Tokyo, both of (JP)

( * ) Notice: Subject to any disclaimer, the term of this patent is extended or adjusted under 35 U.S.C. 154(b) by 0 days.

(21) Appl. No.: 09/274,958

(22) Filed: Mar. 23, 1999

(30) Foreign Application Priority Data

Mar. 31, 1998 (JP) ..... 11-10759

(51) Int. Cl.[7] ..... A01H 5/00
(52) U.S. Cl. ..... Plt./226

(58) Field of Search ..... Plt./226

(56) References Cited

U.S. PATENT DOCUMENTS

P.P. 10,811 * 3/1999 Berry ..... Plt./226

OTHER PUBLICATIONS

Dirr, M.A. Manual of Woody Landscape Plants, p. 1145. Stipes Publishing, Illnois, 1998.*

* cited by examiner

*Primary Examiner*—Bruce R. Campell
*Assistant Examiner*—Melissa L. Kimball
(74) *Attorney, Agent, or Firm*—Armstrong, Westerman, Hattori, McLeland & Naughton, LLP

(57) ABSTRACT

A new variety of *C. scoparius L.* named 'MEI ROAD' is a dwarf shrub suitable for use a potted plant, garden shrub or ground cover.

3 Drawing Sheets

The present invention relates to a new and distinct horticultural variety of *Cytisus scoparius L.*

BACKGROUND OF THE INVENTION

*C. scoparius L.* is a woody shrub of the pulse family originally from Middle Europe and the coast of the Mediterranean Sea. Horticultural varieties of *C. scoparius L.* having various flower colors such as yellow, white, red, cream and mixed colors etc. have been bred. The majority of such varieties are erect and low to slighty tall in height, although there are some which are dwarf such as creeping varieties. Because of the drawback of the required trimming and selection, *C. scoparius L.* is rarely used for ornamental planting.

However, *C. scoparius L.* presents the advantage of vigorous growth even in unfertile wasteland, so if a dwarf variety having a wide variety of flower colors could be bred, its use as a ground cover, ornamental shrub, etc., will be possible, with a wide variety of applications to be expected.

The present inventors have developed a new moderately dwarf variety of *C. scoparius L.* by a combination of mutagenesis by rapid irradiation and tissue culture techniques, as described below:

1. In July 1990, pods of the original species 'CRIMSON KING', formed after 3 weeks of flowering, were externally sterilized in The Institute of Radiation Breeding, National Institute of Agrobiological Resources, Ministry of Agriculture, Forestry and Fisheries, Oomiya-cho, Naka-gun, Ibaraki Pref., Japan. Young embryos removed from these pods were irradiated with gamma rays of Co 60 at 100 Gy for 72 hours.
2. The young embryos thus irradiated were cultivated in an MS agar medium containing plant hormones, (i.e., naphthalene acetic acid and benzyl adenine) at 25° C. for a day length of 16 hours, whereby re-differentiated plants were obtained via multi-blastema and shoots after callus induction.
3. In March 1991, the young plants sufficiently rooted in a sterile medium were transferred to potting media in pots in a greenhouse, then acclimated therein, and transferred to a field.
4. Selection of a dwarf plant from the respective plants was conducted on the basis of plant height, plant width, internode length, etc., as indicators.
5. Evaluation of the practical characteristics of the resulting selected strain was carried out in The Institute of Radiation Breeding, National Institute of Agrobiological Resources, Ministry of Agriculture, Forestry and Fisheries. In reproducing the selected plants, branches were selected from The Institute of Radiation breeding in June; cutting each approximately 10 cm long were planted in sterilized river sand or vermiculite; and rooted plants were cultivated in a mist room. After April 1993, the evaluation was conducted in Ashigara Farm of Meiji Seika Kaisha Ltd. in Kayama, Odawara City, Kanagawa Pref., Japan, and the present *C. scoparius L.* variety, which was judged to be a promising dwarf plant based on the examination results obtained up to May 1997, was finally selected.

The present 'MEI ROAD' variety has a cup-shaped form and moderate dwarfism, which reaches maturation after five years, with a mature height of 90 cm and a mature spread of 40–50 cm. The leaves are sparse and there are more and larger flowers than in the original variety.

BOTANICAL DESCRIPTION

Figure 1:
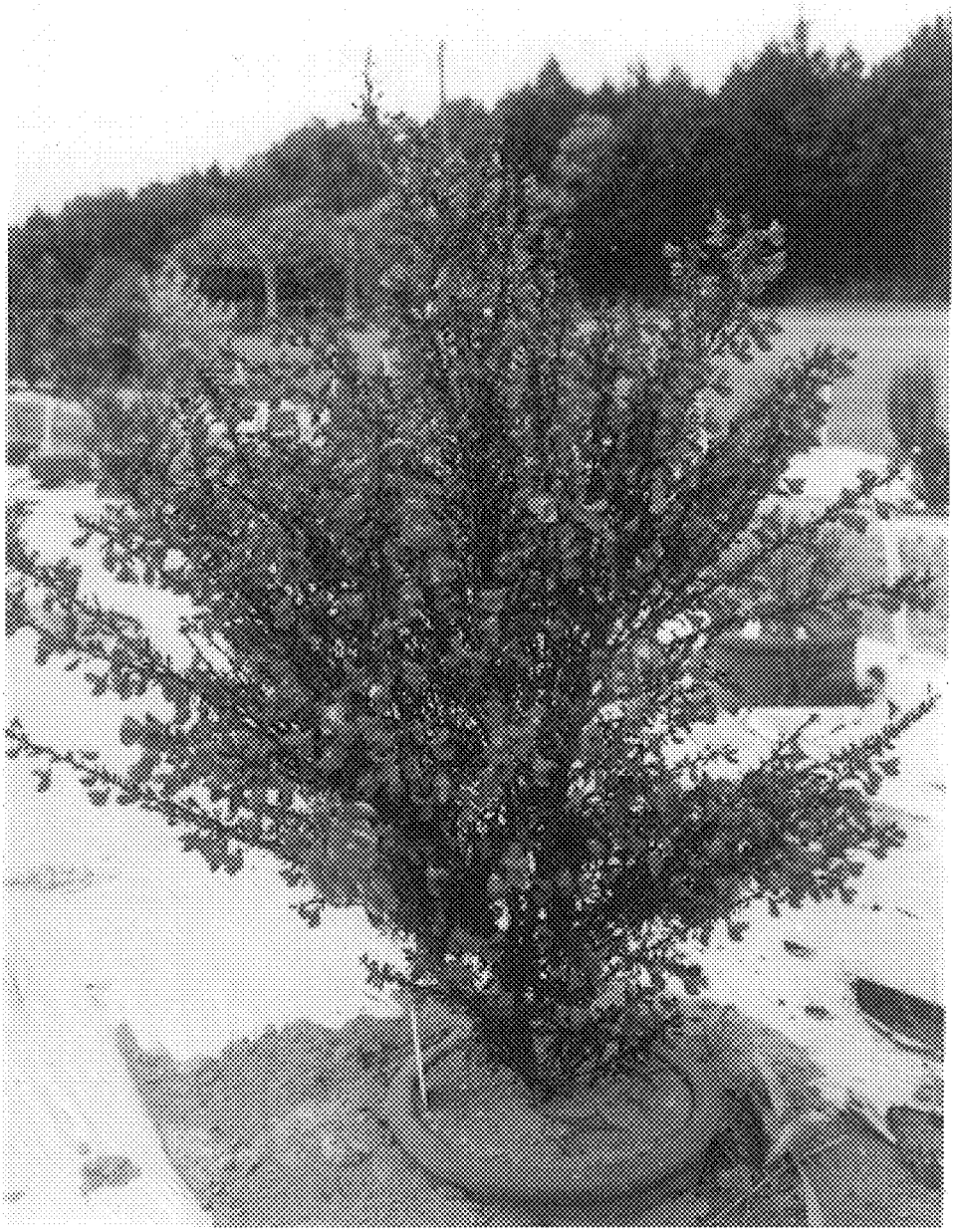
FIG. 1 shows the *C. scoparius L.* variety 'MEI ROAD'.
Figure 2:
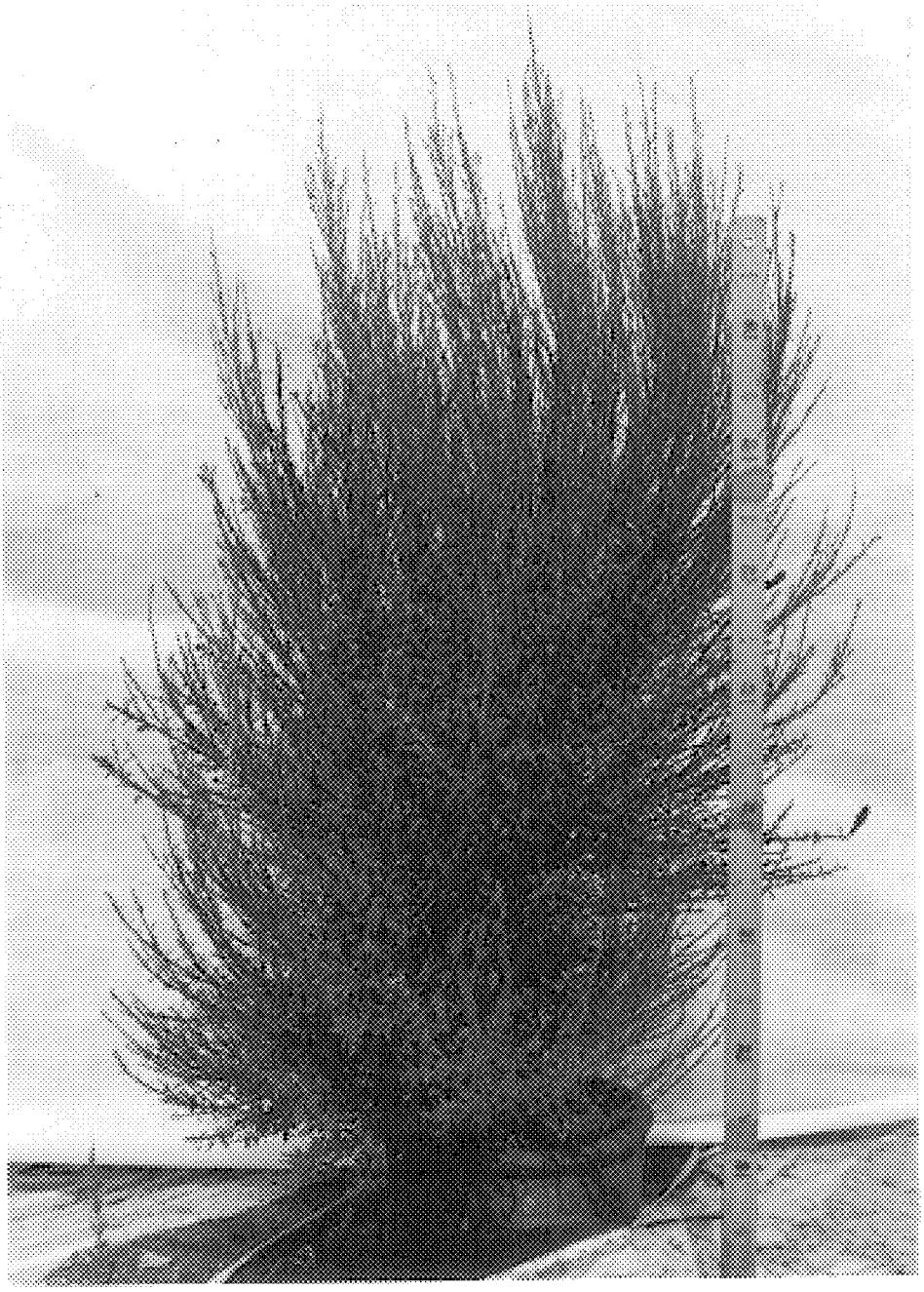
FIG. 2 is a photograph of the variety 'MEI ROAD' at flowering time.
Figure 3:
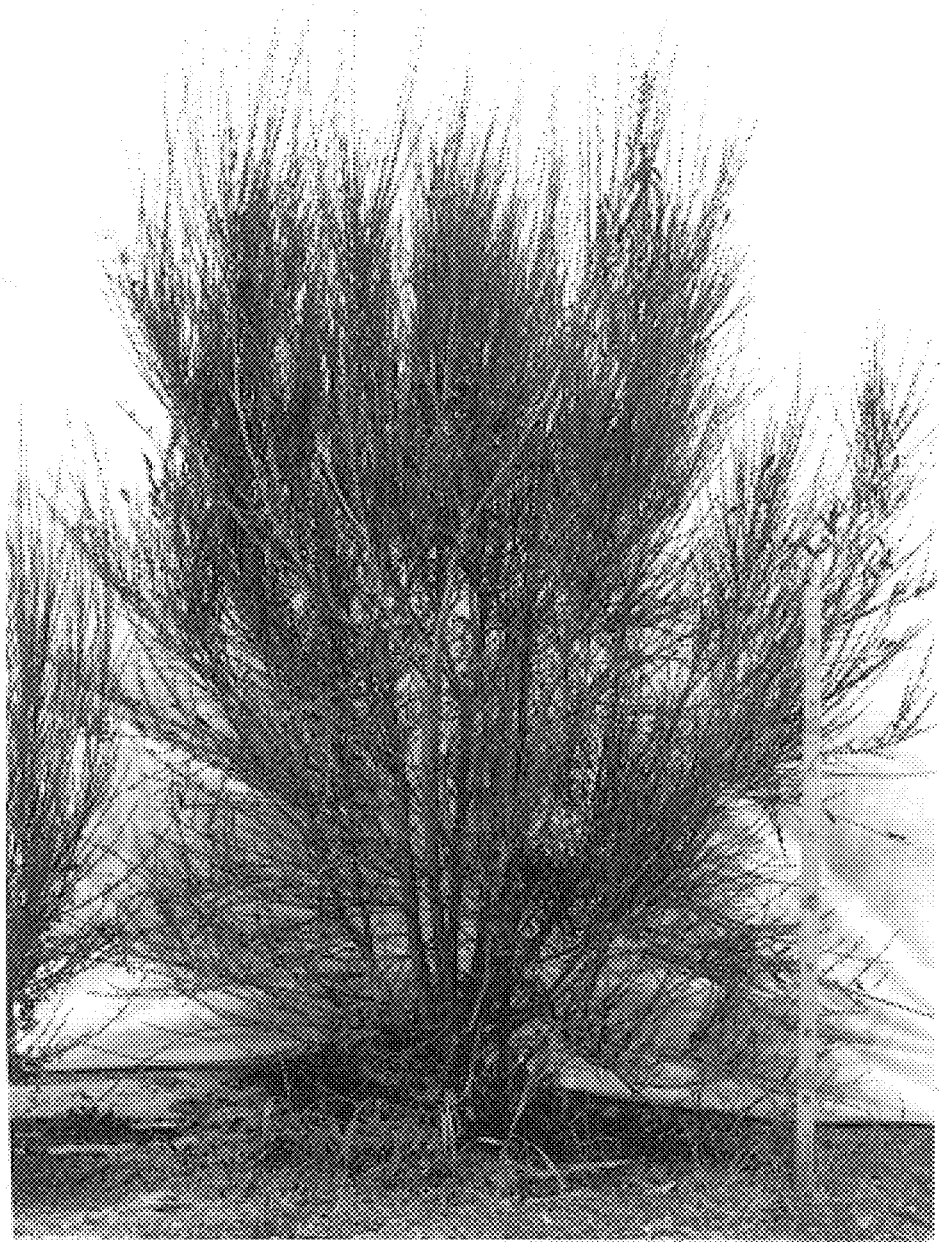
FIG. 3 shows the original variety 'CRIMSON KING'.

The original variety 'CRIMSON KING' is tall, with a plant height of about 160 cm, while 'MEI ROAD' is moderately dwarf, having a mature plant height of about 90 cm. The leaf length and leaf width are 11 cm and 3 mm, respectively, which are shorter than those of the original variety, and the petiole length is also shorter. The leaves are sparse as compared to the original variety.

The flower color is deep red which is almost the same color as in the original variety, the color classified as No. 0414 in the JHS Color Chart which corresponds to RHS 53 B, 179A and 185B. The size of the flower is large as opposed to the original variety which is medium size. That is, the standard petal of the present variety is slightly long having a length of 20.6 mm and a width of 19.1 mm. As compared with the original variety, the wing petal of the present variety has a slightly shorter length of 18.4 mm and a slightly longer width of 9.5 mm. The present variety produces more flowers than the original variety.

The shape of a floral but is long elliptic and its color is deep red. When it blooms, the adaxial face of a standard petal uniformly turn to deep red color, while the abaxial face is light yellow. The adaxial face of a wing petal is deep red while the abaxial face of the wing petal is light yellow. The standard petal and the wing petal of the present variety are comparatively larger than those of the original variety. The overall size of the flower is also larger, and the color of the flower deeper, in comparison to the original variety. Filaments are yellow and curvedly projected from petals with yellow anthers at the tips thereof. Pistils are hidden behind petals and invisible from the outside. The flower emits a fragrance characteristiv of leguminosae. The total bloom period last approximately one month, and the prime of bloom is 7 to 10 days, which is a most valuable term for a decorative plant. Sexual fertility is poor, and few flowers become fertilized. Vegetative propagation by cuttings is required for reproduction.

The distinctive characteristics of 'MEI ROAD' have been examined in plants cultured at Ashigara Farm in the period 1993–1997 as described above, according to the examination standards based on the Japanese Seeds and Seedlings Law. The characteristics of 'MEI ROAD' and the comparative variety 'CRIMSON KING' are described below.

| Characteristic | 'MEI KING' | 'CRIMSON KING' |
|---|---|---|
| Plant vigor | medium | medium to strong |
| Plant form | elliptic | elliptic |
| Plant height | medium (90 cm in 5-year mature plant) | tall to very tall (160 cm) |
| Direction of branching | erect to spreading | erect to spreading |
| Internode length | medium (1.0 cm) | medium (1.1 cm) |
| Leaf composition | mixture of single (one leaflet) and compound (two or three leaflets) in varying ratio | mixture of single (one leaflet) and compound (two or three leaflets) in varying ratio |
| Leaf shape | long elliptic | long elliptic |
| Color of leaf | green | green–deep green |
| Shape of leaf tip | sharp–obutse | sharp–obtuse |
| Shape of leaf edge | smooth | smooth |
| Warp of leaf | convexly warped–flat | convexly warped–flat |
| Length of leaf | short–medium (11.5 mm) | medium–long (12.3 mm) |

-continued

| Characteristic | 'MEI KING' | 'CRIMSON KING' |
|---|---|---|
| Width of leaf | medium (3.0 mm) | medium (3.5 mm) |
| Length of petiole | short–medium (5–10 mm) | medium |
| Leaf | sparse | medium |
| Shape of flower bud | long elliptic | long elliptic |
| Size of flower bud | medium | medium |
| Size of flower | medium–large | medium |
| Color of standard petal (surface) | orange–red JHS: 0414 RHS: 53B; 179A; 185B | red JHS: 0415 RHS: 53C |
| Color of standard petal (back) | white-yellow JHS: 2202 RHS: 18C 19C 20D 158A 162D 164D | white-yellow JHS: 2202 RHS: 18C 19C 20D 158A 162D 164D |
| Color or wing petal (surface) | orange–red JHS: 0414 RHS: 53B; 179A; 185B | red JHS: 0415 RHS: 53C |
| Color of wing petal (back) | white-yellow JHS: 2202 RHS: 18C 19C 20D 158A 162D 164D | white-yellow JHS: 2202 RHS: 18C 19C 20D 158A 162D 164D |
| Length of standard petal | short–medium (20.6 mm) | short (20.1 mm) |
| Width of standard petal | medium (19.1 mm) | medium (17.5 mm) |
| Length of wing petal | short (18.4 mm) | short (19.6 mm) |
| Width of wing petal | narrow (9.5 mm) | narrow (9.1 mm) |
| No. of stamen | medium | medium |
| Branch sprouting time | seasonal, late sprouting begins around March | late |
| Flowering time (70–80%) | average, begins mid-April to mid-May | average |
| Leaf falling time | average, begins around October and completed mid-November | average |
| Disease resistance | no susceptibility to any serious disease, but susceptible to inchworm | |
| Culture | can survive in poor soil if well drained, but root damage if poorly drained. | |

The 'MEI ROAD' cultivar has not been observed under all possible environmental conditions to date. Accordingly, it is possible that the phenotype may vary somewhat with variations in the environment, such as temperature, light intensity, and day length.

We claim:

1. A new and distinct variety of *Cytisus scoparius L.* plant named 'MEI ROAD' substantially as shown and described herein.

* * * * *